US007411115B2

(12) United States Patent
Yu

(10) Patent No.: US 7,411,115 B2
(45) Date of Patent: Aug. 12, 2008

(54) SWEET POTATO SPORAMIN GENE PROMOTER

(75) Inventor: Su-May Yu, Taipei (TW)

(73) Assignee: Academia Sinica, Taipei (TW)

( * ) Notice: Subject to any disclaimer, the term of this patent is extended or adjusted under 35 U.S.C. 154(b) by 333 days.

(21) Appl. No.: 10/989,719

(22) Filed: Nov. 15, 2004

(65) Prior Publication Data

US 2005/0198703 A1 Sep. 8, 2005

Related U.S. Application Data

(63) Continuation-in-part of application No. 10/097,896, filed on Mar. 13, 2002, now abandoned.

(51) Int. Cl.
*A01H 5/00* (2006.01)
*C12N 15/52* (2006.01)
*C12N 15/82* (2006.01)

(52) U.S. Cl. .................... 800/317.2; 800/287; 800/288; 435/419

(58) Field of Classification Search ................. 800/278, 800/288, 298, 317.2; 435/419; 536/23.1, 536/23.2, 23.6, 23.7, 24.1
See application file for complete search history.

(56) References Cited

U.S. PATENT DOCUMENTS

| | | | | |
|---|---|---|---|---|
| 5,110,732 | A | 5/1992 | Benfey et al. | 800/287 |
| 5,436,393 | A | 7/1995 | Rocha-Sosa et al. | 800/287 |
| 2003/0167518 | A1 | 9/2003 | Yeh et al. | |

FOREIGN PATENT DOCUMENTS

| | | | |
|---|---|---|---|
| EP | 0 945 508 | A | 9/1999 |
| EP | 1 348 763 | | 10/2003 |
| JP | 03 072826 | A | 3/1991 |
| TW | 200401031 | | 1/2004 |

OTHER PUBLICATIONS

Shewry P., Annals of Botany, 2003; vol. 91, pp. 755-769.*

Jarret R. L., et al. J. Amer. Soc. Hort. Sci.; 1992, vol. 117, No. 4; pp. 633-637.*

Ohta S. et al. Mol. Gen Genet, 1991; vol. 225, pp. 369-378.*

Hattori T. et al. Plant Molecular Biology, 1988, vol. 11, pp. 417-426.*

Tsukaho Hattori, et al. *Genes coding for the major tuberous root protein of sweet potato: Identification of putative regulatory sequence in the 5' upstream region.* Plant Molecular Biology 11: 417-426, 1998.

Tsukaho Hattori, et al. *High-level expression of tuberous root storage protein genes of sweet potato in stems of plantlets grown in vitro on sucrose medium.* Plant Molecular Biology 14: 595-604, 1990.

Ken Matsuoka, et al. *Propeptide of a precursor to a plant vacuolar protein required for vacuolar targeting.* Proc. Natl. Acad. Sci. USA, 88: 834-838, Feb. 1991.

Kenzo Nakamura, et al. *Processing and Transport to the Vacuole of a Precursor to Sweet Potato Sporamin in Transformed Tobacco Cell Line BY-2.* Journal of Experimental Botany, 44 Supp: 331-337, Jan. 1993.

Shozo Ohta, et al. *High-level expression of a sweet potato sporamin gene promoter: β-glocuroidase (GUS) fusion gene in the stems of transgenic tobacco plants is conferred by multiple cell type-specific regulatory elements.* Mol. Gen. Genet., 225: 369-378, 1991.

Ohta et al. "High-level expression of a sweet potato sporamin gene promoter: beta-glucuroidase (GUS) fusion gene in the stems of transgenic tobacco plants is conferred by multiple cell type-specific regulatory elements". Mol. Gen. Genet 225:369-378, 1991.

Hattori et al. "Genes coding for the major tuberous root protein of sweet potato: identification of putative regulatory sequence of the 5' upstream region". Plant Molecular Biology 11:417-426, 1988.

Morikami et al. "Two cis-acting regulatory elements are involved in the sucrose-inducible expression of the sporamin gene promoter from sweet potato in transgenic tobacco". Mol. Gen. Genomics 272:690-699, 2005.

Wang et al. "Wound-response regulation of the sweet potato sporamin gene promoter region". Plant Molecular Biology 48:223-231, 2002.

Wang et al. "Nucleotide Sequence of a sporamin gene in sweet potato". Plant Physiol. 108:829-830, 1995.

Ohta et al. "High Level Expression of a Sweet Potato Sporamin Gene Promoter: β-glucuroidase (GUS) Fusion Gene in the Stems of Transgenic Tobacco Plants is Conferred by Multiple Cell Type-Specific Regulatory Elements," Mol Gen. Genet. 225:369-378 (1991).

* cited by examiner

*Primary Examiner*—Russell Kallis
(74) *Attorney, Agent, or Firm*—Occhiuti Rohlicek & Tsao LLP

(57) ABSTRACT

A transformed tuberous plant cell or a transgenic tuberous plant containing a heterologous nucleic acid that includes a sweet potato sporamin promoter operably linked to a sequence encoding a polypeptide.

20 Claims, No Drawings

SWEET POTATO SPORAMIN GENE PROMOTER

RELATED APPLICATIONS

This application is a continuation-in-part of and claims priority to U.S. application Ser. No. 10/097,896, filed Mar. 13, 2002 now abandoned, the contents of which are incorporated herein by reference.

BACKGROUND

Sporamin, a storage protein family, accounts for 60-80% of total soluble proteins in the tuberous roots of a sweet potato (Maeshima et al., 1985, Phytochemistry 24: 1899-1902). It is encoded by two major gene subfamilies, A and B (Hatori et al., 1989, Plant Mol Biol 13: 563-572). The genomic DNA of two sporamin genes, SPO-A1 and SPO-B1, have been isolated and characterized (Hattori and Nakamura, 1988, Plant Mol. Biol. 11: 417-426). They belong to the gene subfamilies A and B, respectively.

SUMMARY

The present invention relates to a transformed tuberous plant cell (e.g., a potato cell) containing a heterologous nucleic acid that includes a sweet potato sporamin promoter operably linked to a sequence encoding a polypeptide (e.g., an *Escherichia coli* phytase). The promoter includes a polynucleotide that is at least 96% (e.g., 97%, 98%, 99%, or 100%) identical to nucleotide (nt) −305 to −1 of the SPO-A1 gene (SEQ ID NO: 2, shown below).

```
CATAGACTTCACCTATAGTAAAACCATTGGACACTTGGGCGGCCACAAAT
CATTTCTATTATTTCTCCCAAATCATTTCTGTTATCAACTCTATCTCACC
CCATAAGACACCGTAAGTGTCCCATCCATCGGTCGATCACTGTGTAGTTA
AATCTTCAAGTAGCTAAGTAATTGTGTTTCGCGATGAAAATTCTGAATAC
AAAAAGAGAAAAGCAAAATAATCTTAAAGTTGTACAAGAAACAATAATTC
AACCTTATCTCTTGTTGTCTATAAATTGGATGCATGCATGAGACT
ATGAGAGCCC
```

Example of the sweet potato sporamin promoter include nt −1057 to −1 of the SPO-A1 gene (SEQ ID NO:1, shown below) and its fragments, e.g., SEQ ID NO:2, as long as they retain the capability of initiating transcription.

```
AAGCTTTGCCAAACAGAGCCTAAATCCATCATTTGGATTCACTTATGTGA
ATGAAAGAGAGGGGGCGAAAAGTTAGCTTAATTTACTAATTTGGGTTTTT
ATTTCCAAAGGCCAGAGGAAGGAAAAAGAAAATTAAAAGACATGGCTCTC
CATCGGGTTGCACTCCACCCGTGTGCAGGACAACTTTTACGTTATACAAT
GCAAACTCCTTTAAAATAAATTAAAATCATATATATATAAAATAGTGCAA
CCTATATCACTTTCTCAATGTGGGACGAAGGCACTTTCAAAAGTCTTTCG
AATCCTATTTTTCCTTGAATATATTTCGAGAATAAATTTTTCAATTAATC
ATCATTATCCATCTACGTGTATATATATAATATATATTTCAAATTAAACA
TCTAACTTAGATTTTCCAAAAAAAAAAAACATCTAACTTAGAAGAACCCA
AATTTATTTTTAACTCTACCTATATCAAAAGTGGACTCTACTGAAAATTA
```

-continued

```
TACCACAAAATGATCATTTTAAATGTTATTTTTAACAAAAATTTTAGACA
TTATCTTATTTTAATCTTCTACCGGTTAGAATACTGAAATAAATTTCACT
CATAACATAAATTTGACTAGTGATCGTGAATTTTTACGTAAATTAATCAA
ATAATTGTATGTAATGCAATGGATTTTGATGATGGGTAAAATTTGATGAT
GGGTAAAATATATTTTAATTATTACACTACTTGCCTTCTTTGTTCCTAGG
ATCATAGACTTCACCTATAGTAAAACCATTGGACACTTGGGCGGCCACAA
ATCATTTCTATTATTTCTCCCAAATCATTTCTGTTATCAACTCTATCTCA
CCCCATAAGACACCGTAAGTGTCCCATCCATCGGTCGATCACTGTGTAGT
TAAATCTTCAAGTAGCTAAGTAATTGTGTTTCGCGATGAAAATTCTGAAT
ACAAAAAGAGAAAAGCAAAATAATCTTAAAGTTGTACAAGAAACAATAAT
TCAACCTTATCTCTTGTTGTCTATAAATTGGATGCATGCATGAGACT
ATGAGAGCCC
```

In one embodiment, the sequence encoding the polypeptide is linked to an upstream sequence encoding a propeptide, and the sequence encoding the propeptide is linked to a further upstream sequence encoding a signal peptide. The polypeptide is directed by the signal peptide and the propeptide to vacuoles, where a protein body is formed and the polypeptide is stabilized.

Both the signal peptide and the propeptide may be from a sweet potato sporamin protein, for example, the signal peptide of the SPO-A1 protein, aa 1-21 of the SPO-A1 protein (SEQ ID NO:3) and the propeptide of the SPO-A1 protein, aa 22-37 of the SPO-A1 protein (SEQ ID NO:4). The amino acid sequences of the SPO-A1 signal peptide and propeptide are shown below:

```
                                       (SEQ ID NO:3)
SPO-A1 signal peptide:   MKALTLALFLALSLYLLPNPA

                                       (SEQ ID NO:4)
SPO-A1 propeptide:       HSRFNPIRLPTTHEPA
```

Also within the scope of this invention is a transgenic tuberous plant (e.g., potato) whose genome contains a heterologous nucleic acid that includes a sweet potato sporamin promoter operably linked to a sequence encoding a polypeptide as described above. In such a plant, the polypeptide may be expressed (i.e., at a level higher than that in a non-transgenic plant) in the leaf, stem, and microtuber when cultured in medium, and expressed (i.e., at a level higher than that in a non-transgenic plant) in the leaf, petiole, and tuber when grown in soil.

Tuberous plant cells and tuberous plants express large amounts of recombinant proteins when they contain protein-coding genes under the control of sweet potato sporamin promoters. Such transformed cells and transgenic plants are useful in production of commercially valuable recombinant vaccines and proteins, e.g., phytase widely used in animal feed. The transgenic tuberous plants can also display improved traits by expressing genes involved in, for example, resistance to diseases, insects and stresses; in altering starch or protein content and structures; and in altering nutritional components.

The details of one or more embodiments of the invention are set forth in the accompanying description below. Other features, objects, and advantages of the invention will be apparent from the detailed description, and from the claims.

DETAILED DESCRIPTION

A tuberous plant is a plant that produces tuberous roots, e.g., potato, sweet potato, cassava, carrot, and yam; or a plant that produces tuberous stems, e.g., taro, onion, and lily. Among the tuberous plants, potato is of particular interest as it serves as a major food crop in many countries and is widely used in food, animal feed, and other industries.

The present invention is based on the discovery that a sweet potato sporamin promoter directs high expression of a recombinant protein when it is introduced into a tuberous plant cell, for example, via *Agrobacterium*-mediated transformation. Specifically, this invention features a transformed tuberous plant cell containing a heterologous nucleic acid that includes a sweet potato sporamin promoter operably linked to a sequence encoding a polypeptide. A "heterologous" nucleic acid, gene, or protein is one that originates from a foreign species, or, if from the same species, is substantially modified from its original form. For example, a sweet potato sporamin promoter operably linked to a heterologous coding nucleic acid sequence is one form of a sequence heterologous to sweet potato. If a promoter and a coding sequence are from the same species, one or both of them are substantially modified from their original forms.

Sweet potato sporamin proteins are encoded by a gene family. In the examples described below, an SPO-A1 promoter, bp −1057 to −1 of the SPO-A1 gene (SEQ ID NO:1) is used to direct the expression of an *Escherichia coli* phytase in a transformed potato cell. This promoter can be substituted by any other promoter within the sweet potato sporamin family, or by a shorter promoter sequence which is capable of initiating transcription, e.g., bp −305 to −1 of the SPO-A1 gene (SEQ ID NO:2).

Sporamin accumulates in large quantities in vacuoles of the tuberous root of sweet potato. It is synthesized as a prepro-precursor with a 21-amino acid signal peptide and a 16-amino acid propeptide at the N-terminus (Matsuoka and Nakamura, 1991, Proc. Natl. Acad. Sci. USA 88: 834-838). The signal peptide and the propeptide are required for vacuolar targeting of sporamin (Matsuoka et al., 1990, J. Biol. Chem. 265: 19750-19757).

Thus, when a sweet potato sporamin promoter is introduced into a tuberous plant cell to direct the expression of a recombinant polypeptide, the sequence encoding the polypeptide can be linked to an upstream sequence encoding a propeptide, the coding sequence of which is linked to a further upstream sequence encoding a signal peptide. Both the propeptide and the signal peptide are from a sweet potato sporamin protein. The propeptide and the signal peptide can be from the same sweet potato sporamin protein (e.g., the SPO-A1 protein); they can also be from two different members of the sporamin protein family. The polypeptide is directed by the signal peptide and the propeptide to vacuoles and accumulates there. Vacuolar localization allows the polypeptide to form a protein body and becomes more stable, thereby resulting in high yields of the recombinant polypeptide.

The transformed tuberous plant cell described above can be cultivated to become a transgenic plant. Unexpectedly, the polypeptide is highly expressed in various organs of a transgenic plant either cultured in medium or grown in soil, which has low concentration sugar (e.g., no greater than 3%). For instance, in a transgenic potato expressing an *Escherichia coli* phytase under the control of an SPO-A1 promoter, 6% of the soluble proteins in the leaf and stem and 3% of the soluble proteins in the tuber are phytase proteins (see the examples below). As such, the entire transgenic potato, including the leaf, stem, and tuber, can be processed and used as an animal feed additive at reduced production costs.

The specific examples below are to be construed as merely illustrative, and not limitative of the remainder of the disclosure in any way whatsoever. Without further elaboration, it is believed that one skilled in the art can, based on the description herein, utilize the present invention to its fullest extent. All publications recited herein are hereby incorporated by reference in their entirety.

Materials and Methods

1. Plant Materials

In vitro cultured potato (*Solanum tuberosum L.* cv. Kennebec) seedlings and microtubers were used. The potato seedlings were initiated by culture of 2-3-cm stem segments on MS agar medium (Murashige and Skoog, 1962, Physiol Plant 15: 473-497). The potato microtubers were produced by culturing root-containing 2-3-cm stem segments on a modified MT agar medium (Wang and Hu, 1982, American Potato J 59: 33-37) that contains MS salts with 10 mg/L 6-BAP and 8% sucrose. The cultures were maintained at 25° C. with a 16-hr daily light.

2. PCR

A 1057-bp sporamin gene (SPO-A1) promoter, a 63-bp signal peptide sequence, and a 48-bp propeptide sequence were PCR-amplified using sweet potato genomic DNA as a template and oligo-nucleotides Spo5' (5'-CCCAAGCTTTGCCAAACAGAGCCTA-3' (SEQ ID NO:5), HindIII site underlined) and Spopro3' (5'-GGAATTCGGCGGGTTCGTGTGTGGT-3' (SEQ ID NO:6), EcoRI site underlined) as primers. The Spo5' and Spopro 3' primers were designed based on a genomic DNA sequence of SPO-A1 (Hattori and Nakamura, 1988, Plant Mol. Biol. 11: 417-426). A nopaline synthase gene (Nos) terminator was PCR-amplified using pBI221 (Clontech) as a DNA template and oligo-nucleotides 5'-TCCGAGCTGCAGATCGTTCAAACATTT-3' (SEQ ID NO:7) (PstI site underlined) and 5'-AGCGAGCTCGATCGATCTCTAGACAT-3' (SEQ ID NO:8) (ClaI and XbaI sites underlined) as forward and reverse primers, respectively. The *E. coli* phytase gene appA was PCR-amplified using plasmid pET-appA (Golovan et al., 2000, Can J Microbiol 46: 59-71) as a DNA template and oligo-nucleotides appA 5' (5'-AAAGAATTCCAGAGTGAGCCGGAGCTGAAGCT-3', (SEQ ID NO:9) EcoRI site underlined) and appA 3' (5'-AAACTGCAGTTACAAACTGCACGCCGGTAT-3' (SEQ ID NO:10) PstI site underlined) as forward and reverse primers, respectively. pET-appA was a gift from the Department of Microbiology, University of Guelph, Canada.

3. Plasmid Construction

The PCR-amplified sequence of sporamin gene promoter, the signal peptide, and the propeptide was digested with HindIII and EcoRI, and subcloned into the same sites in pBluescript (Strategene) to generate pBS-Spopro. The PCR-amplified Nos terminator was digested with PstI and XbaI and fused downstream of the sporamin propeptide sequence in pBS-Spopro to generate pBS-Spopro-Nos. The PCR-amplified appA gene was digested with EcoRI and PstI and inserted into the same sites in pBS-Spopro-Nos to generate pBS-Spopro-appA-Nos. The Spopro-appA-Nos chimeric gene was excised from pBS-Spopro-appA-Nos with XbaI and HindIII and inserted into the same sites of the binary vector pCAMBIA2301 (a gift from Richard A. Jefferson, CAMBIA, Australia) to generate pSpopro-appA. The junction regions which link PCR-amplified DNA fragments were all verified by DNA sequencing.

4. Bacterial Strains

Plasmid pSpopro-appA was transferred into *E. coli* strain XL1-blue (Stratagene) and *Agrobacterium tumefaciens* strain LBA4404 (Hoekema et al., 1983, Nature 303: 179-180) using electroporation. Phytase activity was detected in the transformed *E. coli* and *Agrobacteriuim* using a modified agar plate phytase activity assay method (Yanke et al., 1998, Microbiology 144: 1565-1573; also see below), indicating that the sporamin gene promoter was recognized and active phytase was correctly produced by the two bacteria.

5. Transformation

The potato microtubers were sliced into discs of 2-mm thickness. Discs were placed on 3C5ZR agar medium (Sheerman and Bevan, 1988, Plant Cell Reports 7: 13-16) in a Petri dish and co-cultured with *Agrobacterium* in 5 ml of 3C5ZR liquid medium. The culture was incubated at 26° C. for 15 min. The microtubers were transferred to 3C5ZR-AS agar medium (3C5ZR medium with 100 μM acetosyringon (Aldrich) and 3 g/L phytagel (Sigma), pH 5.2) and incubated at 28° C. in dark for 72 hr. The infected microtuber discs were washed three times with 3C5ZR liquid medium containing 100 mg/L ticarcillin/clavulanicacid (timenten) (Duchefa), blotted dry on sterile filter papers, and transferred to 3C5ZR agar medium containing 100 mg/L each of kanamycin (Sigma) and timenten and incubated at 26° C. with 16-hr daily light for selection of transformants. The tissues were subcultured at weekly intervals. After several weeks, the young shoots formed from the inoculated microtuber discs were transferred to MS agar medium containing 100 mg/L each of kanamycin and timenten and incubated at 26° C. with 16-hr daily light. The regenerated seedlings of 10-15-cm high were transferred to soil and incubated at 26° C. with 16-hr daily light for further growth.

6. Overexpression of Phytase Encoded by appA in *Pichia pastoris* and Preparation of Antibodies The coding region of appA was PCR-amplified using a pET- appA as the DNA template and oligo-nucleotides 5'-GCGAATTCCAGAGTGAGCCGGAGCTG-3' (SEQ ID NO:11) (EcoRI site underlined) as the 5' primer and 5'-GCTCTAGATACGCATTAGACAGTTCTTCGTT-3' (SEQ ID NO:12) (XbaI site underlined) as the 3' primer. The PCR product was digested with EcoRI and XbaI and ligated into the same sites in pICZαA (Invitrogen) to generate pPICZαA-appA. appA was led by a signal peptide of α-factor and was under the control of alcohol oxidase (AOX) promoter. pPICZαA-appA was amplified in *Escherichia coli* DH5α (Promega) grown in low salt LB broth (1% tryptone, 0.5% sodium chloride, 0.5% yeast extract, pH 7.5) supplemented with Zeocin (25 μg/ml) (Invitrogen). pPICZαA-appA was linearized by restriction enzyme PmeI digestion and transferred into *P. pastoris* host strain KM71 (Invitrogen) by electroporation. The transformed cells were plated on YPD (1% yeast extract, 2% peptone, 2% dextrose, 1 M sorbitol, pH 7.5) supplemented with zeocin (100 μg/ml) at 30° C. for 3 days. Zeocin-resistant yeast colonies were incubated in BMGY medium (1% yeast extract, 2% peptone, 1 mM potassium phosphate, pH 6.0, 1.34% yeast nitrogen bath (Invitrogen), $4\times10^{-5}$% biotin, and 1% glycerol) for enrichment of cell mass and then in BMMY medium (same ingredients as BMGY medium except that 1% glycerol was replaced with 0.5% methanol) for induction of phytase expression. All media were prepared according to the protocols provided in the EasySelect *Pichia* Expression Kit (Invitrogen).

Phytase was the major protein secreted into the culture medium, and was recovered by lyophilization of the culture medium. One hundred micrograms of purified phytase was injected into a New Zealand White rabbit successively at 4 to 6-day intervals to generate polyclonal antibodies according to the methods described by Williams et al. (Expression of foreign proteins in *E. coli* using plasmid vectors and purification of specific polyclonal antibodies (1995) In: DNA Cloning 2. Expression Systems. A Practical Approach. (Ed) Glover D M and Hames B D. IRL Press, New York).

7. Western Blot Analysis

Total proteins were extracted from the microtuber, leaf, and petiole of a potato plant using an extraction buffer (50 mM Tris-HCl (pH 8.8), 1 mM EDTA, 10% glycerol, 1% Triton X-100, 10 mM β-mercaptoethanol, and 0.1% sarkosyl). Western blot analysis was performed using an ECL Western blotting analysis system (Amersham Pharmacia) according to the manufacturer's instructions.

8. Phytase Activity Assay

Protein extract was prepared from the microtuber, leaf, and petiole of a potato plant as described by Li et al. (1997, Plant Physiol 114: 1103-1111). The phytase activity was determined as described by Shimizu (1992, Biosci Biotech Biochem 56: 1266-1269). One unit of phytase activity was defined as the amount of enzyme that frees 1 μmole inorganic P from 1.5 mM-sodium phytate/min at pH 4.5 and 37° C.

Results

1. Generation of Transgenic Potato Plants

A 1057-bp sporamin gene promoter, a 63-bp sequence encoding a 21-amino acid signal peptide, and a 48-bp sequence encoding a 16-amino acid propeptide from sweet potato were placed upstream of the coding region of appA gene to make a translational fusion, and the nopaline synthase gene (Nos) terminator was placed downstream of the appA coding region. The chimeric DNA was then inserted into the binary vector pCAMBIA2301 to generate pSpopro-appA, which was delivered into potato genome via *Agrobacterium*-mediated transformation of potato microtuber discs. The putative transgenic lines were selected on medium containing kanamycin.

Approximately 15 independent putative transgenic plants were regenerated and cultured for microtuber production. Expression of phytase gene in transformed potatoes was confirmed by blot analysis of RNA purified from microtubers. As pSpopro-appA also contains a CaMV35S-GUS cDNA fusion gene derived from pCAMBIA2301, expression of GUS was determined by GUS activity staining assay of leaves. GUS activity was detected in leaves of transformed potato lines but not in leaves of a non-transformed control. These results indicate that the phytase and GUS genes have been integrated into the genomes of transformed potato lines.

2. Sweet Potato Sporamin Gene Promoter Confers High Level Expression of Phytase in Leaf, Stem and Microtuber of Transgenic Potato Cultured in Medium Total proteins were extracted from leaves, stems, roots and microtubers of two transgenic potato lines 1-1 and 2-1 cultured in medium and subjected to Western blot analysis using the phytase antibody described above. Unexpectedly, phytase with correct molecular weight of 48 kD was accumulated at high levels in leaves, stems and microtubers and at low levels in roots. Phytase was not detected in non-transformants. A 34-kD protein was also detected in the transgenic lines with the phytase antibody. The 34-kD protein could be a degradation product of the 48-kD phytase, since it is not present in non-transformants.

Phytase activity in various organs of transgenic potato lines 1-1, 2-1 and another line 7-1 was also determined. The results show that phytase activity correlates well with the expression level of phytase, i.e., phytase activity is also high in leaves, stems and microtubers but low in roots. Phytase activity was not detected in non-transformants.

3. Sweet Potato Sporamin Gene Promoter Confers High Level Expression of Phytase in Tuber of Transgenic Potato Grown in Soil Transgenic potato plants were transferred to pots in growth chamber and allowed to form tubers. Total proteins were extracted from tubers of six transgenic lines and subjected to Western blot analysis using the phytase antibody. Unexpectedly, the 48-kD phytase accumulated in all six transgenic lines but not in non-transformants. The level of the 34-kD protein detected by the phytase antibody was lower in the tubers of soil-grown transgenic potatoes than in the leaves, stems and microtubers of transgenic potatoes cultured in medium.

Total proteins were extracted from leaves, petioles and tubers of transgenic potato lines 1-1, 2-1, and 7-1, and phytase activity was analyzed. Phytase activity was detected in all organs of the transgenic lines but not in non-transformants. Unexpectedly, phytase activity was 3-5-fold higher in tubers than in leaves and petioles.

4. High Yield of Phytase in Leaf, Stem and Tuber of Transgenic Potato

Total proteins were extracted from leaves, stems and tubers of transgenic potato lines 1-1, 2-1, and 7-1, and subjected to Western blot analysis using the phytase antibody described above. Various known amounts of phytase purified from the culture medium of *Pichia* were used as the quantification standards. Unexpectedly, the yields of phytase in leaves and stems were approximately 6% of total soluble proteins, and the yield of phytase in tubers was approximately 3% of total soluble proteins. These yields are comparable to the high yield of phytase expressed in canola seeds under the control of cruciferin A promoter (Verwoerd and Pen, 1996, Phytase produced in transgenic plants for use as a novel feed additive. In Transgenic Plants: A Production System for Industrial and Pharmaceutical Proteins. Eds. M. R. L. Owen and J. Pen. John Wiley & Sons Ltd. p. 213-225).

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the following claims.

What is claimed is:

1. A transformed tuberous plant cell comprising a heterologous nucleic acid that contains a sweet potato sporamin promoter operably linked to a sequence encoding a polypeptide, wherein the sweet potato sporamin promoter includes SEQ ID NO:1.

2. The transformed tuberous plant cell of claim 1, wherein the polypeptide is an *Escherichia coli* phytase.

3. The transformed tuberous plant cell of claim 1, wherein the sequence encoding the polypeptide is linked to an upstream sequence encoding a propeptide, and the sequence encoding the propeptide is linked to a further upstream sequence encoding a signal peptide, wherein both the propeptide and the signal peptide are from a sweet potato sporamin protein.

4. The transformed tuberous plant cell of claim 3, wherein the signal peptide is SEQ ID NO:3 and the propeptide is SEQ ID NO:4.

5. The transformed tuberous plant cell of claim 1, wherein the tuberous plant is potato.

6. The transformed tuberous plant cell of claim 5, wherein the polypeptide is an *Escherichia coli* phytase.

7. The transformed tuberous plant cell of claim 5, wherein the sequence encoding the polypeptide is linked to an upstream sequence encoding a propeptide, and the sequence encoding the propeptide is linked to a further upstream sequence encoding a signal peptide, wherein both the propeptide and the signal peptide are from a sweet potato sporamin protein.

8. The transformed tuberous plant cell of claim 7, wherein the signal peptide is SEQ ID NO:3 and the propeptide is SEQ ID NO:4.

9. A transgenic tuberous plant whose genome comprises a heterologous nucleic acid that contains a sweet potato sporamin promoter operably linked to a sequence encoding a polypeptide, wherein the sweet potato sporamin promoter includes SEQ ID NO:1.

10. The transgenic tuberous plant of claim 9, wherein the polypeptide is an *Escherichia coli* phytase.

11. The transgenic tuberous plant of claim 9, wherein the sequence encoding the polypeptide is linked to an upstream sequence encoding a propeptide, and the sequence encoding the propeptide is linked to a further upstream sequence encoding a signal peptide, wherein both the propeptide and the signal peptide are from a sweet potato sporamin protein.

12. The transgenic tuberous plant of claim 11, wherein the signal peptide is SEQ ID NO:3 and the propeptide is SEQ ID NO:4.

13. The transgenic tuberous plant of claim 9, wherein the polypeptide is expressed in the leaf, stem, and microtuber of the transgenic tuberous plant cultured in medium.

14. The transgenic tuberous plant of claim 9, wherein the polypeptide is expressed in the leaf, petiole, and tuber of the transgenic tuberous plant grown in soil.

15. The transgenic tuberous plant of claim 9, wherein the tuberous plant is potato.

16. The transgenic tuberous plant of claim 15, wherein the polypeptide is an *Escherichia coli* phytase.

17. The transgenic tuberous plant of claim 15, wherein the sequence encoding the polypeptide is linked to an upstream sequence encoding a propeptide, and the sequence encoding the propeptide is linked to a further upstream sequence encoding a signal peptide, wherein both the propeptide and the signal peptide are from a sweet potato sporamin protein.

18. The transgenic tuberous plant of claim 17, wherein the signal peptide is SEQ ID NO:3 and the propeptide is SEQ ID NO:4.

19. The transgenic tuberous plant of claim 15, wherein the polypeptide is expressed in the leaf, stem, and microtuber of the transgenic tuberous plant cultured in medium.

20. The transgenic tuberous plant of claim 15, wherein the polypeptide is expressed in the leaf, petiole, and tuber of the transgenic tuberous plant grown in soil.

* * * * *

SEQUENCE LISTING

```
<160> NUMBER OF SEQ ID NOS: 12

<210> SEQ ID NO 1
<211> LENGTH: 1057
<212> TYPE: DNA
<213> ORGANISM: Ipomea batatas

<400> SEQUENCE: 1

aagctttgcc aaacagagcc taaatccatc atttggattc acttatgtga atgaaagaga      60

gggggcgaaa agttagctta atttactaat ttgggttttt atttccaaag gccagaggaa     120

ggaaaaagaa aattaaaaga catggctctc catcgggttg cactccaccc gtgtgcagga     180

caacttttac gttatacaat gcaaactcct ttaaaataaa ttaaaatcat atatatataa     240

aatagtgcaa cctatatcac tttctcaatg tgggacgaag gcactttcaa aagtctttcg     300

aatcctattt ttccttgaat atatttcgag aataaatttt tcaattaatc atcattatcc     360

atctacgtgt atatatataa tatatatttc aaattaaaca tctaacttag attttccaaa     420

aaaaaaaaac atctaactta gaagaaccca aatttatttt taactctacc tatatcaaaa     480

gtggactcta ctgaaaatta taccacaaaa tgatcatttt aaatgttatt tttaacaaaa     540

attttagaca ttatcttatt ttaatcttct accggttaga atactgaaat aaatttcact     600

cataacataa atttgactag tgatcgtgaa tttttacgta aattaatcaa ataattgtat     660

gtaatgcaat ggattttgat gatgggtaaa atttgatgat gggtaaaata tattttaatt     720

attacactac ttgccttctt tgttcctagg atcatagact tcacctatag taaaaccatt     780

ggacacttgg gcggccacaa atcatttcta ttatttctcc caaatcattt ctgttatcaa     840

ctctatctca ccccataaga caccgtaagt gtcccatcca tcggtcgatc actgtgtagt     900
```

-continued

```
taaatcttca agtagctaag taattgtgtt tcgcgatgaa aattctgaat acaaaaagag    960

aaaagcaaaa taatcttaaa gttgtacaag aaacaataat tcaaccttat ctcttgttgt   1020

ctataaattg gatgcatgca tgagactatg agagccc                             1057


<210> SEQ ID NO 2
<211> LENGTH: 305
<212> TYPE: DNA
<213> ORGANISM: Ipomea batatas

<400> SEQUENCE: 2

catagacttc acctatagta aaaccattgg acacttgggc ggccacaaat catttctatt     60

atttctccca aatcatttct gttatcaact ctatctcacc ccataagaca ccgtaagtgt    120

cccatccatc ggtcgatcac tgtgtagtta aatcttcaag tagctaagta attgtgtttc    180

gcgatgaaaa ttctgaatac aaaaagagaa aagcaaaata atcttaaagt tgtacaagaa    240

acaataattc aaccttatct cttgttgtct ataaattgga tgcatgcatg agactatgag    300

agccc                                                                305


<210> SEQ ID NO 3
<211> LENGTH: 21
<212> TYPE: PRT
<213> ORGANISM: Ipomea batatas

<400> SEQUENCE: 3

Met Lys Ala Leu Thr Leu Ala Leu Phe Leu Ala Leu Ser Leu Tyr Leu
 1               5                  10                  15

Leu Pro Asn Pro Ala
            20


<210> SEQ ID NO 4
<211> LENGTH: 16
<212> TYPE: PRT
<213> ORGANISM: Ipomea batatas

<400> SEQUENCE: 4

His Ser Arg Phe Asn Pro Ile Arg Leu Pro Thr Thr His Glu Pro Ala
 1               5                  10                  15


<210> SEQ ID NO 5
<211> LENGTH: 25
<212> TYPE: DNA
<213> ORGANISM: Artificial Sequence
<220> FEATURE:
<223> OTHER INFORMATION: Primer

<400> SEQUENCE: 5

cccaagcttt gccaaacaga gccta                                           25


<210> SEQ ID NO 6
<211> LENGTH: 25
<212> TYPE: DNA
<213> ORGANISM: Artificial Sequence
<220> FEATURE:
<223> OTHER INFORMATION: Primer

<400> SEQUENCE: 6

ggaattcggc gggttcgtgt gtggt                                           25


<210> SEQ ID NO 7
<211> LENGTH: 27
```

-continued

<212> TYPE: DNA
<213> ORGANISM: Artificial Sequence
<220> FEATURE:
<223> OTHER INFORMATION: Primer

<400> SEQUENCE: 7
tccgagctgc agatcgttca aacattt 27

<210> SEQ ID NO 8
<211> LENGTH: 26
<212> TYPE: DNA
<213> ORGANISM: Artificial Sequence
<220> FEATURE:
<223> OTHER INFORMATION: Primer

<400> SEQUENCE: 8
agcgagctcg atcgatctct agacat 26

<210> SEQ ID NO 9
<211> LENGTH: 32
<212> TYPE: DNA
<213> ORGANISM: Artificial Sequence
<220> FEATURE:
<223> OTHER INFORMATION: Primer

<400> SEQUENCE: 9
aaagaattcc agagtgagcc ggagctgaag ct 32

<210> SEQ ID NO 10
<211> LENGTH: 30
<212> TYPE: DNA
<213> ORGANISM: Artificial Sequence
<220> FEATURE:
<223> OTHER INFORMATION: Primer

<400> SEQUENCE: 10
aaactgcagt tacaaactgc acgccggtat 30

<210> SEQ ID NO 11
<211> LENGTH: 26
<212> TYPE: DNA
<213> ORGANISM: Artificial Sequence
<220> FEATURE:
<223> OTHER INFORMATION: Primer

<400> SEQUENCE: 11
gcgaattcca gagtgagccg gagctg 26

<210> SEQ ID NO 12
<211> LENGTH: 31
<212> TYPE: DNA
<213> ORGANISM: Artificial Sequence
<220> FEATURE:
<223> OTHER INFORMATION: Primer

<400> SEQUENCE: 12
gctctagata cgcattagac agttcttcgt t 31